United States Patent

Osorio et al.

(10) Patent No.: US 8,515,538 B1
(45) Date of Patent: *Aug. 20, 2013

(54) MEDICAL DEVICE FAILURE DETECTION AND WARNING SYSTEM

(75) Inventors: Ivan Osorio, Leawood, KS (US); Mark G. Frei, Lawrence, KS (US); Naresh C. Bhavaraju, Lenexa, KS (US)

(73) Assignee: Flint Hills Scientific, LLC, Lawrence, KS (US)

( * ) Notice: Subject to any disclaimer, the term of this patent is extended or adjusted under 35 U.S.C. 154(b) by 1271 days.

This patent is subject to a terminal disclaimer.

(21) Appl. No.: 12/157,955

(22) Filed: Jun. 13, 2008

Related U.S. Application Data

(62) Division of application No. 10/982,748, filed on Nov. 5, 2004, now Pat. No. 7,389,144.

(60) Provisional application No. 60/518,027, filed on Nov. 7, 2003.

(51) Int. Cl.
*A61N 1/08* (2006.01)

(52) U.S. Cl.
USPC ........ 607/29; 600/300; 607/2; 607/1; 607/27; 607/63

(58) Field of Classification Search
USPC .......................................... 607/29, 28, 17, 18
See application file for complete search history.

(56) References Cited

U.S. PATENT DOCUMENTS

| | | | |
|---|---|---|---|
| 3,805,796 A | 4/1974 | Terry et al. | |
| 4,024,875 A | 5/1977 | Putzke | |
| 4,102,346 A | 7/1978 | Fulker | |
| 4,345,603 A | 8/1982 | Schulman | |
| 4,445,512 A | 5/1984 | Krupka et al. | |
| 4,488,555 A * | 12/1984 | Imran | 607/29 |
| 5,197,468 A | 3/1993 | Proctor et al. | |
| 5,571,141 A | 11/1996 | McNeil et al. | |
| 5,873,898 A | 2/1999 | Hemming et al. | |
| 5,891,180 A | 4/1999 | Greeninger et al. | |
| 5,904,708 A | 5/1999 | Goadeke | |
| 6,067,473 A | 5/2000 | Greeninger et al. | |
| 6,247,474 B1 | 6/2001 | Greeninger et al. | |
| 6,341,236 B1 | 1/2002 | Osorio et al. | |
| 6,450,172 B1 | 9/2002 | Hartlaub et al. | |
| 6,571,128 B2 | 5/2003 | Lebel et al. | |
| 7,389,144 B1 * | 6/2008 | Osorio et al. | 607/29 |
| 2002/0065540 A1 | 5/2002 | Lebel et al. | |

* cited by examiner

*Primary Examiner* — Carl H Layno
*Assistant Examiner* — Jon Eric C Morales

(57) ABSTRACT

A failure detection and warning system for monitoring a medical device wherein the system includes means structured to passively or actively detect faults occurring in the medical device being monitored, and wherein the fault includes an unprogrammed and/or undesired shut off of the medical device being monitored or an unprogrammed and/or undesired shut-off of the output of the medical device being monitored by the system.

25 Claims, 6 Drawing Sheets

MEDICAL DEVICE FAILURE DETECTION AND WARNING SYSTEM

CROSS REFERENCE TO RELATED APPLICATION

This application is a divisional of U.S. application Ser. No. 10/982,748 filed Nov. 5, 2004, now U.S. Pat. No. 7,389,144; which claims priority of provisional patent application No. 60/518,027 filed Nov. 7, 2003.

BACKGROUND OF THE INVENTION

1. Field of the Invention

The present invention relates to medical devices and, more specifically without limitation, to implanted medical devices.

2. Description of the Related Art

The advent of microprocessors has stimulated proliferation of implantable medical devices for monitoring and treatment of cardio-vascular and neurological diseases; examples of such devices are cardiac pacemakers, implantable cardioverter defibrillators (ICDs), nerve stimulators, brain stimulators for Parkinson's disease and tremor therapy, pain therapy stimulators, spinal cord stimulators, cochlear stimulators, prostheses, infusion pumps, and devices for warning of seizures, syncope or falls. Verification of the functional status of these devices can be obtained through user-initiated interrogation or in the case of battery status, automatically. Despite their technical sophistication, unintentional or accidental shut off, or non-user programmed changes in recording/detection or stimulation parameters (e.g., caused by radiation, electromagnetic or electrostatic discharges, and power line interference) remain as serious, unaddressed problems. Of all these potential problems, inadvertent or accidental shut-off of the device or of its output is the most difficult to address because of its unpredictability and also the most serious because of the consequences these failures may have on subjects with potentially fatal cardiac or neurological diseases; this is particularly true if their manifestations are intermittent and unpredictable, as is the case with cardiac arrhythmias and seizures. Envision, for instance, the outcome of inadvertent shut-off caused by, for example, electromagnetic interference of an implantable defibrillator, demand pacemaker, or of a seizure blockage device. Consideration of any of these possible scenarios leads to the inevitable conclusion that the ability to automatically and without delay detect and warn the user about device failure is potentially a life-saving feature, regardless of the mode of operation (continuous or intermittent) of the device. The inability of present state-of-the-art devices to automatically detect failure is particularly egregious, especially for devices programmed to operate only in response to specific events, such as demand pacemakers, ICDs, and certain neuro-stimulators. While causes of accidental shut-off of a device's power or of its output have been identified and patients are instructed about potential hazards and safety issues regarding exposure to sources of electromagnetic energy, it is very difficult, if patients are to lead a normal life, to avoid these sources and the risk of accidental interference with the normal operation of the device. To summarize, in spite of the highly advanced features programmed or built into state-of-the-art medical devices, none have the capability to immediately and automatically detect and communicate the occurrence of failures or of improper functioning to the user.

A schematic representation of a prior art implantable medical device is depicted in FIG. 1. When turned on, the prior art devices start with some default parameters, which are then modified by physicians or other qualified personnel to suit a particular mode of operation. These devices then generally operate in this mode for several weeks or sometimes even years. Basic automated checks for low battery, lead integrity, and memory accessibility exist for many of these devices. A schematic representation of a typical failure of a prior art implantable medical device, which can occur at any time in a prior art device, is depicted in FIG. 2. Failures are most dangerous and most likely to occur when the device is conducting an unsupervised operation, which is generally the predominant operating mode of such devices. Once failures or faults occur, they may remain undetected until the next scheduled user-initiated interrogation or the occurrence of a serious or fatal adverse event, whichever occurs first.

The prior art in the area of device status diagnostics provides means to inform the user of impending delivery of electrical currents, changes in programmed parameters (identifiable only during interrogation) and low battery by using audible or visible alarms, low-voltage "tickler" stimulation, or vibration, but no means to detect accidental device or output shut-off and report them as soon as they occur. For example, U.S. Pat. Nos. 4,024,875, 4,488,555, 4,345,603, 4,445,512, and 4,102,346 disclose means for detecting and warning about low battery or low voltage. Several other patents, namely U.S. Pat. Nos. 6,067,473, 6,450,172, 5,891,180, and 6,247,474, mention using audible signals to deliver messages related to low battery, impending delivery of therapy, and acknowledgement of programming to user, but none of these patents provides a method or program for automatically detecting and warning the user, without delay, that the monitoring/therapeutic medical device has failed or that the output has been shut-off. U.S. Pat. No. 5,197,468 discloses a different approach via attaching a protective device to reduce the effects of RF or electrostatic energy on a medical device which, although useful, does not provide patients with the necessary protection and warning in case of failure. There are devices on the market (e.g., Marquis® Family of ICDs from Medtronic, Inc.) that have self-monitoring patient alert systems (Expanded Patient Alert™) for certain kinds of problems, such as improper programming, out of range parameters, low battery and faulty leads. U.S. Pat. No. 3,805,796 discloses means, using externally generated pulses and internal counters, to prevent extraneous signals from changing any device parameter by accident but, if an unplanned change does occur, there are no means to detect these changes and warn the user. Other methods for fault detection are given in U.S. Pat. No. 5,571,141 wherein a secondary circuit takes over when a specific fault is detected in a primary circuit. That method, however, is very specific to this invention because the secondary circuit is essentially and operationally the same as the primary and thus not generalizable. Similarly, Patent Application Publication No. 20020065540 discloses methods that detect some failures and provide alarms. For example, that patent application discloses the use of two redundant ICs, which must be in agreement for delivery of a drug to occur. Some of the alarm conditions are low battery, empty reservoir, and hardware failure, such as CPU failure using a periodic watch dog timer and over/under delivery of drug. However, that patent application does not disclose or teach how to detect and warn automatically of a device output shutoff or of a device reset, specifically if the fault is not associated with hardware failure. Another, U.S. Pat. No. 6,453,196, discloses methods for detecting abnormal behavior of timing circuits in a medical device by using two different clocks and comparing their pulse counts, but it does not address non-timer-related problems, such as failure of output or accidental reset. All of the above-cited prior art devices fail to operate as programmed when the devices are shut off or are reset accidentally or when the primary output of the devices fail due to external disturbances such as electromagnetic interference, electrostatic interference, radiation or some other unknown reason.

What is needed is a failure detection and warning system having means structured to passively or actively detect faults occurring in a medical device wherein the fault includes an unprogrammed and/or undesired shut off of the medical device or an unprogrammed and/or undesired shut-off of the output of the medical device.

SUMMARY OF THE INVENTION

The improvements of the present invention include a system for the detection, warning and logging, via a diary, of implantable medical device failures. The present invention provides methods and systems that in various different applications operate autonomously from the medical device being monitored, including providing a warning or alarm, e.g., sound, light or vibration, and/or maintain a log (e.g., date, time and duration) when there is an unprogrammed or accidental device shut off or failure. Another embodiment of the present invention detects, warns and/or logs interference, such as electromagnetic energy that may affect the normal operation of the medical device.

PRINCIPAL OBJECTS OF THE INVENTION

The principal objects and advantages of the present invention include: providing an automatic failure detection and warning system; providing such a system that monitors the status of various medical devices; providing such a system that monitors the functions of various medical devices; providing such a system that operates autonomously from the medical device or devices being monitored; providing such a system that has an independent power source; providing such a system that is constructed in such a manner that it cannot be shut down by an unprogrammed event; providing such a system that is constructed in such a manner that it cannot be shut down by environmental interference or noise; providing such a system that requires a specific sequence of commands ('key') for disablement; providing such a system that is configured such that its warning, logging and any other programmed functions are automatically activated by non-user (unplanned or unprogrammed) shutoff of either the medical device being monitored or of the output of the medical device; providing such a system that monitors or interrogates at prescribed points in time, either periodically, randomly, continuously, or on cue, the status and/or functions of the medical device for conformity with programmed values/modes of operation; providing such a system that monitors or interrogates the medical device at prescribed points in time, either periodically, randomly, continuously, or on cue, to ascertain the status of pre-specified states or functions and issues a warning/alarm if the medical device or its output have been shut-off accidentally or unintentionally, or if values/parameters or modes of operation or functions do not conform to those which have been programmed into the medical device; providing such a system that takes a cue from the medical device or from sensors and, in response thereto, checks the status of pre-specified states and/or observed behavior of the medical device for conformity with user-programmed parameters/values or modes of operation; provides such a system that monitors a medical device and performs certain pre-specified tasks, e.g., failure warning, logging of medical device failures or other medical device states, etc., if it detects an unexpected, unprogrammed, or undesirable behavior; providing such a system that generates appropriate warnings in the event of unauthorized or unexpected operation or faults and, in response thereto, may trigger a second set of operations such as resetting the medical device; providing such a system that maintains a log or diary to record and store the date, time, duration and/or description of undesirable events internal or external to the medical device, such as those which the medical device detects, e.g., detection of cardiac fibrillation, and those which the medical device can not detect, e.g., faults; providing such a system that monitors the input of closed-loop devices whose operation, especially for therapy delivery, depends on the integrity of the input, e.g., if the input is interrupted or its quality is poor, an alarm is issued; and generally providing such a system that that is reliable in performance, capable of long lasting life, and particularly well adapted for the proposed usages thereof.

Other objects and advantages of this invention will become apparent from the following description taken in conjunction with the accompanying drawings wherein are set forth, by way of illustration and example, certain embodiments of this invention.

BRIEF DESCRIPTION OF THE DRAWING FIGURES

Figure 1:
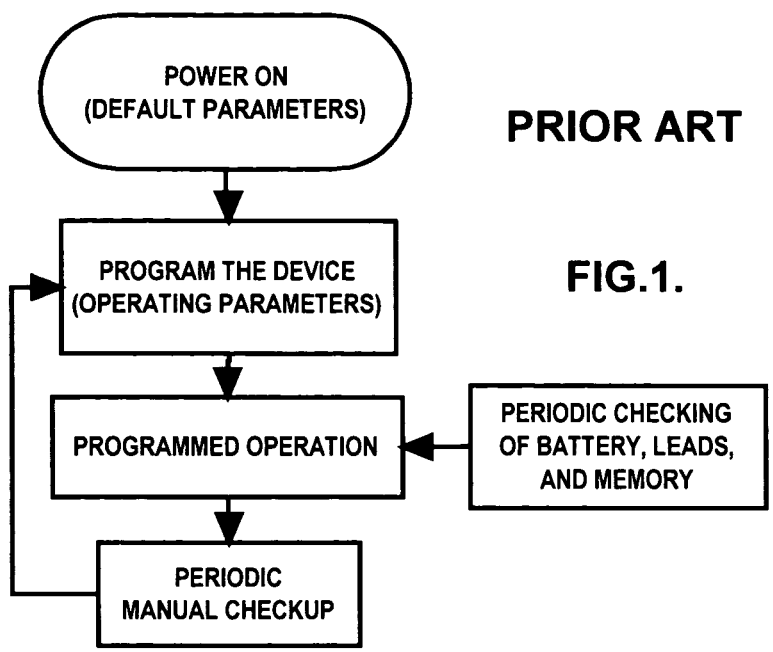
FIG. 1 is a schematic representation of a prior art implantable medical device.

FIGS. 5A-D depict examples of circuits that can be used by the failure detection and warning system of the present invention to detect failure of a medical device.

DETAILED DESCRIPTION OF THE PREFERRED EMBODIMENTS

The present invention includes a failure detection and warning system ("FDWS") for automatic detection/logging and warning of any unprogrammed, undesirable shut-off and faults of medical devices, either presently available in the marketplace, in the process of being designed/developed, or those to be designed or developed in the future. The functions of the FDWS include, but are not limited to, monitoring, warning, resetting, and logging of medical device failures and the date/time they occur. Although for simplicity the discussion of the invention herein will primarily be limited to use of the FDWS in conjunction with a single medical device, it is to be understood that one or more FDWS may be used with a multiplicity of medical devices.

In one embodiment of the present invention, see Table 1, the FDWS is powered ON by the user, either independently of a medical device being monitored by the FDWS, or automatically and simultaneously with the activation or reset of the medical device; the functions of the FDWS remain on STANDBY around the clock when the power to the medical device is ON and the outputs of the medical device are enabled or ON. If either the power or the output of the medical device is accidentally or inadvertently turned OFF or disabled, the FDWS can be configured to issue an alarm/warning when this change occurs, and other relevant functions, such as corrective actions, including but not limited to resetting of the medical device, are performed as programmed. Those skilled in the art will appreciate that the FDWS may have as many sub-systems as the

TABLE 1

States of the FDWS in a preferred embodiment and a medical device.

| Medical Device | FDWS | FDWS Functions |
| --- | --- | --- |
| Device On | ON | Standby |
| Output On | ON | Standby |
| Device Off (uprogrammed or unplanned) | ON | ON (or activated) |
| Output Off (unprogrammed or unplanned) | ON | ON (or activated) | medical device has functions or outputs. For example, a particular circuit may be under the control of the output status of the medical device so that when the output is enabled, the function of this circuit is turned to STANDBY and accidental shut-off of the output automatically switches the circuit from STANDBY to ON, so that a warning may be issued and appropriate corrective actions implemented to restore the device to normal functioning. Non-user-programmed changes in parameters or function, among others, may be monitored via such a passive mode of the FDWS.

In another embodiment of the present invention, the FDWS monitors or interrogates, either continuously, periodically, randomly or on cue, outputs or functions of the medical device or its parameters. While the power to the FDWS remains ON and the FDWS continues to operate autonomously from the medical device, depending on the application or mode of operation of the medical device, the FDWS may go into a dormant state to decrease power consumption. For example, if the FDWS is programmed to periodically interrogate the medical device, the FDWS may go into a dormant state in between interrogations. Interrogation of the medical device by the FDWS may also be triggered by using the output of electromagnetic energy sensors. Sensing of electromagnetic energy in excess of a programmable threshold, above which the medical device may be adversely affected, is used to trigger an alert or other action by the FDWS.

In the case where the FDWS is to monitor a "closed-loop" or feedback-dependent medical device, monitoring the presence and quality of the input to the medical device can be performed to help ensure proper function and the FDWS may operate in the manners hereinbefore described while also sensing the input to the medical device. The FDWS can obtain access to this medical device input and operation in many ways including, but not limited to, the following:

1) Utilization of a "Y-type" connector, or some other type of connector that carries to the FDWS (without delay) the identical input(s), or some representation of those input(s), that the medical device receives. It is to be understood that this monitoring should be performed in a manner that does not adversely affect the input information to the medical device that would be received in the absence of the FDWS monitoring. These inputs shared between the medical device and the FDWS, whether electrical or optical, for example, may be monitored with appropriate sensors at the FDWS entry port to assess their integrity without significant modification of the input to the medical device;

2) Utilization of sensors to enable the FDWS to non-invasively detect electrical/electromagnetic fields, changes in temperature, acoustic signals for monitoring the status of certain functions of the medical device;

3) Incorporation of a receiver into the FDWS, wherein the receiver is configured to listen to telemetry or other wireless communication to the medical device from one or more sensors, a medical device programming or interrogating device, or other any other source of input to the medical device; and 4) When practical and feasible, configure the medical device to communicate this input to the FDWS via telemetry or other means for monitoring and, if needed, for resetting purposes.

The FDWS may also obtain information regarding the status of the medical device by means of an interrogation mechanism in which the FDWS may issue requests for information or other inputs to the medical device and monitor the response.

Interrogation of a medical device by the FDWS requires an interface, which may consist of hardware, software, or a combination of both, and the degree of complexity thereof depends upon the particular application.

The FDWS may be configured to include an internal clock or timer. If a medical device does not respond to interrogation within a pre-specified period of time, the FDWS can initiate a programmed action. For example, an alarm can be automatically activated or, if a response of the medical device reveals faults or parameters or functions outside programmed values/modes, the alarm/warning as well as corrective functions/measures are automatically activated and a surveillance cycle restarted. On the other hand, if the response of the medical device is timely and all parameters/modes of operations checked by the FDWS are as programmed, then the surveillance cycle continues.

In another embodiment of the present invention, a medical device is configured to issue status reports to the FDWS, either continuously, periodically, randomly, or on cue.

In this case, the FDWS is configured to include a processor, memory, and software, hardware, and/or firmware sufficient to perform a comparison between information received from the medical device and a programmed set of expected or allowable range of associated values. A comparator routine is then used to determine relevant deviations. If the FDWS does not receive a report in accordance with the prevailing routine, or if the report does not match programmed values/functions, i.e., it shows deviations, the FDWS issues a warning and corrective measures. If the report is timely and it matches expected values, FDWS functions remain on STANDBY.

Those skilled in the art can appreciate that the embodiments described herein may work in parallel, for example, with redundant surveillance and that the FDWS may be located within the same housing as the medical device, or that the FDWS may be located external to the medical device or even external to the subject.

The FDWS may be configured to monitor an existing medical device leaving the architecture of the medical device unchanged, or modification of the medical device may be required to enable interrogation or monitoring. It should be noted that if a communication interface already exists in the medical device, it can be accessed by the FDWS and a new one may not need to be developed. Examples of operation of the FDWS include, but are not limited to: a) sensing medical device outputs, e.g., electrical stimulation, by the FDWS and taking readings from medical device test points, e.g., battery, clock, or other parameter information that the medical device as originally designed may provide to an external system that do not interfere with normal medical device operation; and b) obtaining detailed information about internal workings of the medical device, outputs from the medical device in response to interrogation requests from the FDWS, etc. Many communication schemes/protocols and developed hardware and software interfaces already exist that are well known to those skilled in the art that would be adequate for this purpose.

The FDWS can detect non-user programmed/undesirable faults such as shut-off of the medical device or of an output of the medical device by performing the following tasks:

(a) check "ON" status of the medical device;
(b) check to determine if outputs of the medical device are enabled;
(c) interrogate the medical device to obtain relevant information regarding other parameters or functions; sensors may also be used in addition to or instead of interrogation routines or protocols;
(d) process and analyze the medical device by using the processor/controller of the medical device for each response or information obtained from the medical device and determine if the state/status of the medical device is normal/desirable, i.e., in conformance with expected, programmed behavior;
(e) if faults or deviations are detected, the FDWS issues a warning/alarm, takes corrective measures, downloads and stores to a non-volatile memory the type, date, time and/or durations of the fault event, and may also store the time(s) of any automatic or manual fault corrections;
(f) once the fault has been corrected, the FDWS either resets itself to start a new surveillance cycle, or logs the correction and ceases associated warnings, while continuing to monitor for subsequent faults; and
(g) if no fault or deviation is detected, the device continues its surveillance in any available mode, i.e., periodically in the case of an open-loop device, or on cue in the case of a closed-loop device.

There may be a hierarchy of monitoring tasks employed by the FDWS for efficiency, placing determination of whether the medical device is ON or OFF as highest priority, determination of whether the output of the medical device is enabled or disabled as next highest priority, and other determinations at equal or lower priorities. Monitoring for these or other different types of failures may be compartmentalized and operate in parallel, so fault detection can be as early as possible. Warnings of the FDWS may reflect the seriousness and type of the failure or deviation. For example, a warning associated with shut-off of the medical device or disablement of its output may be more intense and distinct from that triggered by the proximity of the medical device to electromagnetic interference or a radio frequency source.

The FDWS may be constructed/configured to be substantially more resistant or virtually immune to electro-magnetic or any other type of interference than is the medical device monitored by the FDWS, since this may not be possible to achieve, or as easy to engineer, or as cost effective, in a medical device, given the fact that the functions of the medical device may, in general, be more complex than the FDWS and, as such, require more components, often longer and more connections, and a larger housing with less flexibility in terms of placement and size, factors which may make it more vulnerable to exogenous sources of interference. For example, the FDWS may include double casing, proper shielding and grounding, electromagnetic interference filters, and the use of a programmed software key to make it much more resistant to interference or faults than the medical device being monitored. Those skilled in the art can appreciate that, when feasible, the medical device may incorporate one or more of these features into its design but, even in such a case, if any failure mode for the medical device remains that can be ascertained by the FDWS, the need for the FDWS is not obviated. The FDWS may additionally be programmed to deliver a sensory stimulation, a beep, or some such indication, periodically (e.g. once a day) to indicate that the FDWS is working properly. This feature, in addition to the aforementioned immunity to external disturbances, ensures failsafe operation of the FDWS.

Another embodiment of the FDWS is configured to include a means for actively probing the medical device to ascertain its functional state. This may be especially useful in the absence of pre-existing compatible hardware or software communication means between the FDWS and the medical device. Such active probing, unlike the passive monitoring using sensors to pick up signals generated by the medical device while in operation, could, for example, deliver electromagnetic or acoustic signals to the medical device and effect some sort of expected output. The FDWS can then check to see if the observed output/response of the medical device conforms to the expected output to determine if the medical device is functioning properly in this regard. For example, if the medical device is intended to provide a brief electrical stimulation in response to detected brain activity of a certain type, the FDWS can be configured to produce a small current that mimics the brain activity, such that it can be detected and trigger stimulation by the medical device. The FDWS then performs a check to determine whether or not this medical device stimulation actually occurs and if not, a failure of the medical device is detected.

Whichever embodiment is being utilized, the FDWS tasks described herein may operate automatically when the medical device is turned ON, e.g. Power On Reset, and such tasks may be executed continuously, periodically, randomly, at prespecified time-points, or on cue, i.e., enabled by a specific event or by a delay in initiating or successfully completing a task. For example, the detection of the onset of a pathological state such as an epileptic seizure or of an undesirable transition between physiological states, e.g., from wakefulness to drowsiness while operating a vehicle, may cause a program to look for specific preprogrammed markers which include, but are not limited to, commands or parameter values, and/or verify that tasks such as delivery of therapy, or of warning of an impending change in state have taken place. In the case of electrical stimulation, the FDWS may look for a stimulation artifact which, if not found, will trigger issuance of a warning that the medical device has malfunctioned and perform an event logging. This can be accomplished, for example, using an algorithm for analyzing voltage signals in a processor in a manner that enables the detection as an artifact, such as the algorithm for detection of vagus nerve stimulation artifact as disclosed in U.S. Pat. No. 6,341,236B1, which is incorporated herein by reference in its entirety. Similarly, the above-listed steps may also start if a sensor, such as an electromagnetic pulse sensor, detects electromagnetic noise. The steps hereinbefore described may be performed independently of each other or in any order that may best serve a specific purpose.

To accomplish the above tasks, the FDWS may have a processor, non-volatile memory, a clock or timer, and means of communication from and to the medical device and to other local or remote devices, e.g., relays for remote warning, calling 911 or other centralized monitoring service, activating lights, speakers, external processors for additional analysis of data, remote adverse event logging, a user interface, such as one or more event buttons, etc.

Figure 2:
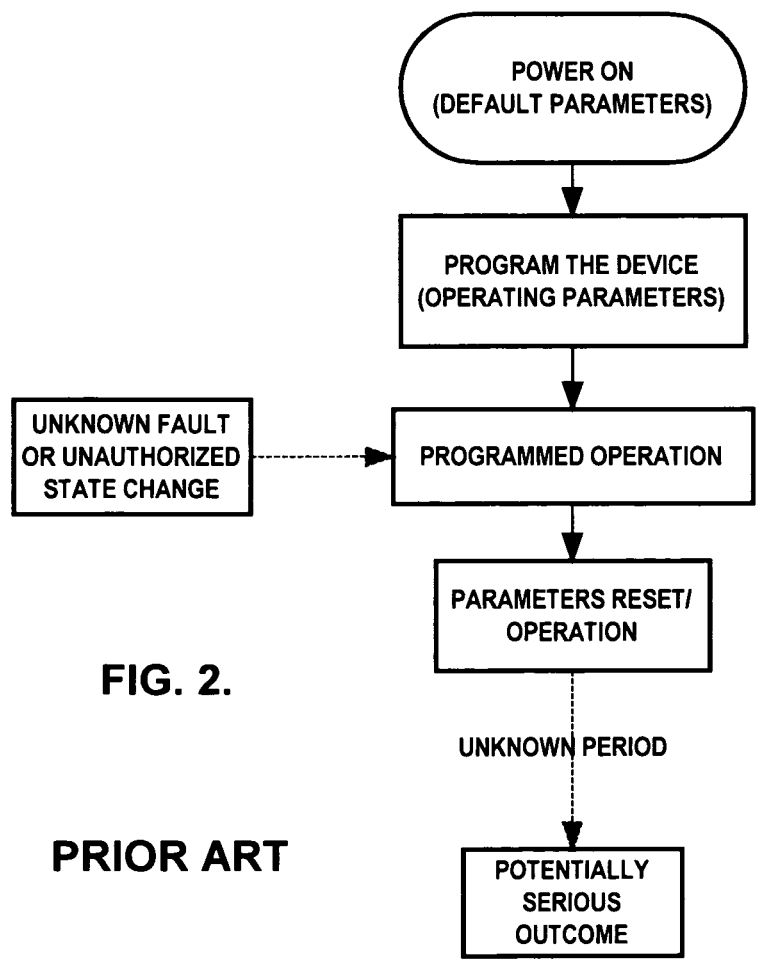
FIG. 2 is a schematic representation of a typical failure of a prior art implantable medical device.

FIG. 1 depicts the normal operation of a prior art medical device. The parameters that are loaded into the medical device when it is switched ON are called the default parameters. These parameters are typically configured to make the medical device as safe as possible, which often corresponds to "No Therapy Delivery" in the case of therapeutic medical devices, or very basic monitoring in case of diagnostic medical devices. These medical devices are then programmed by a physician or another qualified practitioner to operate in a way that is best suited for a particular subject. Once a medical device is programmed and tested, it is generally left unsupervised for variable periods of time, sometimes weeks or even months. Most available medical devices have basic fault detection modules, such as for low battery, lead integrity, and memory errors. FIG. 2 depicts how an unforeseen event can lead to a failure or to a fault in the operation of a medical device, i.e., output is turned OFF which in currently existing medical devices without the benefit of the present invention, may go undetected because of lack of appropriate diagnostic tools and means to warn the user in a timely manner of the occurrence of an adverse device event.

Figure 3:
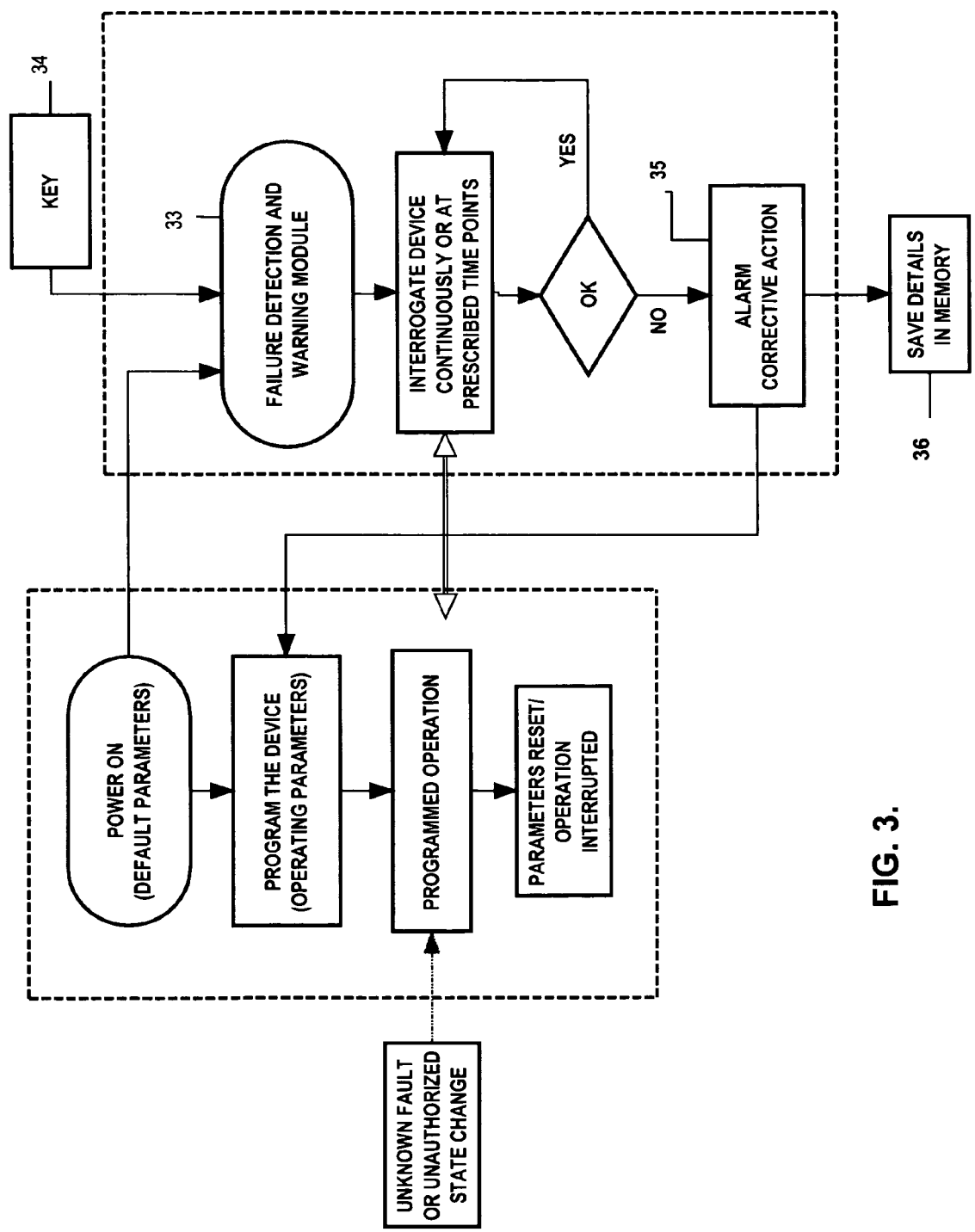
FIG. 3 depicts one of several possible methods for device failure detection, according to the present invention.

FIG. 3 depicts an embodiment of the invention in which the FDWS communicates bi-directionally with a medical device. The system and methods of this embodiment consist of software and/or hardware that run as part of the FDWS, autonomously from the medical device and check the status of the medical device continuously, upon reset of the medical device, periodically, randomly, and/or on some other cue. As the status of the medical device is monitored, upon detecting unauthorized changes to program parameters or other discrepancies, the FDWS sends out alarms or takes corrective actions 35. The FDWS 33 is programmed so that it may only be shut off upon receiving a very specific sequence of commands, key 34, such that the probability of an FDWS malfunction as a result of some random event, such as an electrostatic or electromagnetic pulse or radiation, is negligible. The FDWS can be programmed via telemetry or other suitable means. Anytime the FDWS needs to be shut off, the user has to provide a password or perform a sequence of steps before the FDWS accepts the command to shut off. Further, before the FDWS shuts off, it stores the key (or any other pass code) in a non-volatile memory. This key 34 may be configured to be outside the architecture and control of the medical device. This non-volatile memory is checked when the FDWS is started or reset to ensure the FDWS was properly shut down in the previous session, and then this memory is erased. The FDWS is designed to automatically check its non-volatile memory when the FDWS is started or reset; the FDWS gives an alarm upon restart if the key 34 is not present as expected in the non-volatile memory 36. Those skilled in the art can appreciate that simple state-monitoring circuits similar to ones disclosed in this application can be designed to be attached the FDWS to activate an alarm or an LED if the FDWS is shut off without the key. For example, these circuits can use an output pin of the FDWS to determine the state of FDWS. These operations prevent the FDWS from being shut down inadvertently and enable logging and warning of any shut down of FDWS that is unexpected. This feature of the FDWS substantially reduces the probability of the FDWS being shut off accidentally and, combined with shielding thereof from electro-magnetic interference or other external noise sources, makes probability of failure of the FDWS negligible, unlike that of the medical device that the FDWS is designed to monitor. The FDWS may also contain a clock and memory 36 that may be used to log the different events that occur during the life of the medical device, accomplishing the task of a diary. This diary can log failure information that the FDWS detects and/or may provide redundant logging of information transferred to the FDWS from the medical device.

The information about the state of the medical device that can be monitored by the FDWS can be divided into two sets: (i) that which is accessible/observable by the FDWS without requiring any modification of the medical device, and (ii) that which requires modification of the medical device to enable the FDWS to access the medical device. Examples of the first set may include, but are not limited to, available outputs, test points, battery voltage, and/or any information accessible using any existing communication interface of the medical device. The FDWS may be configured to incorporate subsystems or components such as sensors or sensing modules that detect the type of outputs (including noise/artifacts) generated by the medical device. These may include, for example, sensors for electromagnetic fields, acoustic activity, vibrations, or temperature changes. Also, the FDWS may be configured to monitor whether therapy has been delivered and whether the delivery occurred in a timely matter and according to pre-specified parameters. Electromagnetic sensors may be used to detect stimulation artifact or microdialysis subsystems, or other means, to detect and measure concentrations of various substances in tissue.

Figure 4A:
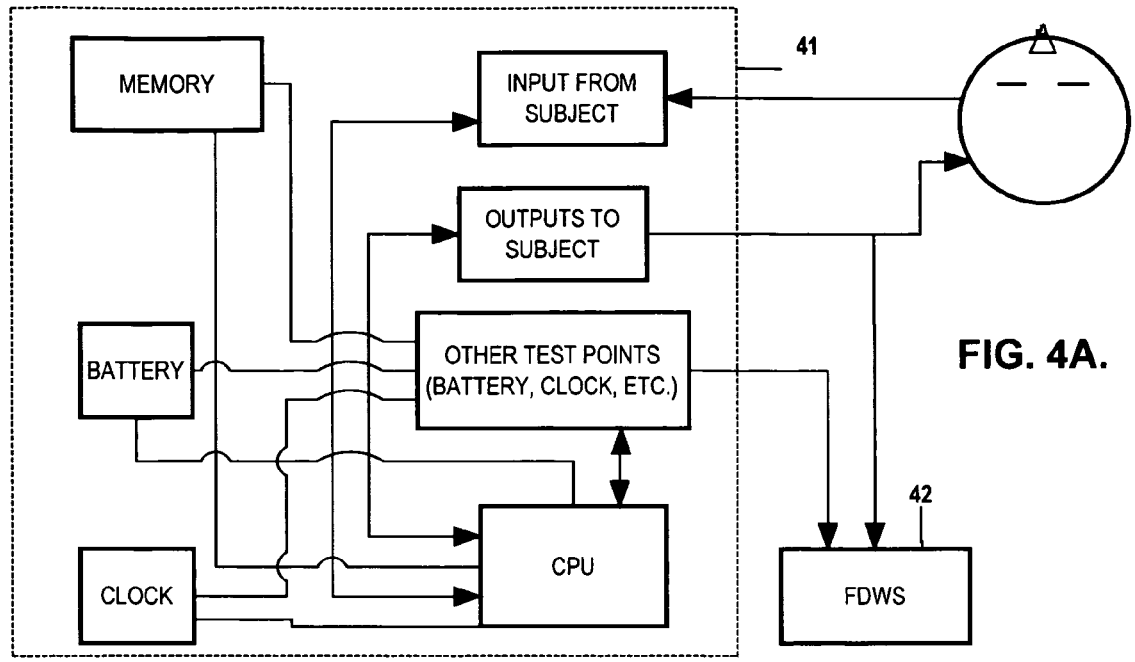
FIG. 4A depicts device failure detection wherein a medical device is being monitored by the failure detection and warning system of the present invention without modification of a medical device.
Figure 4B:
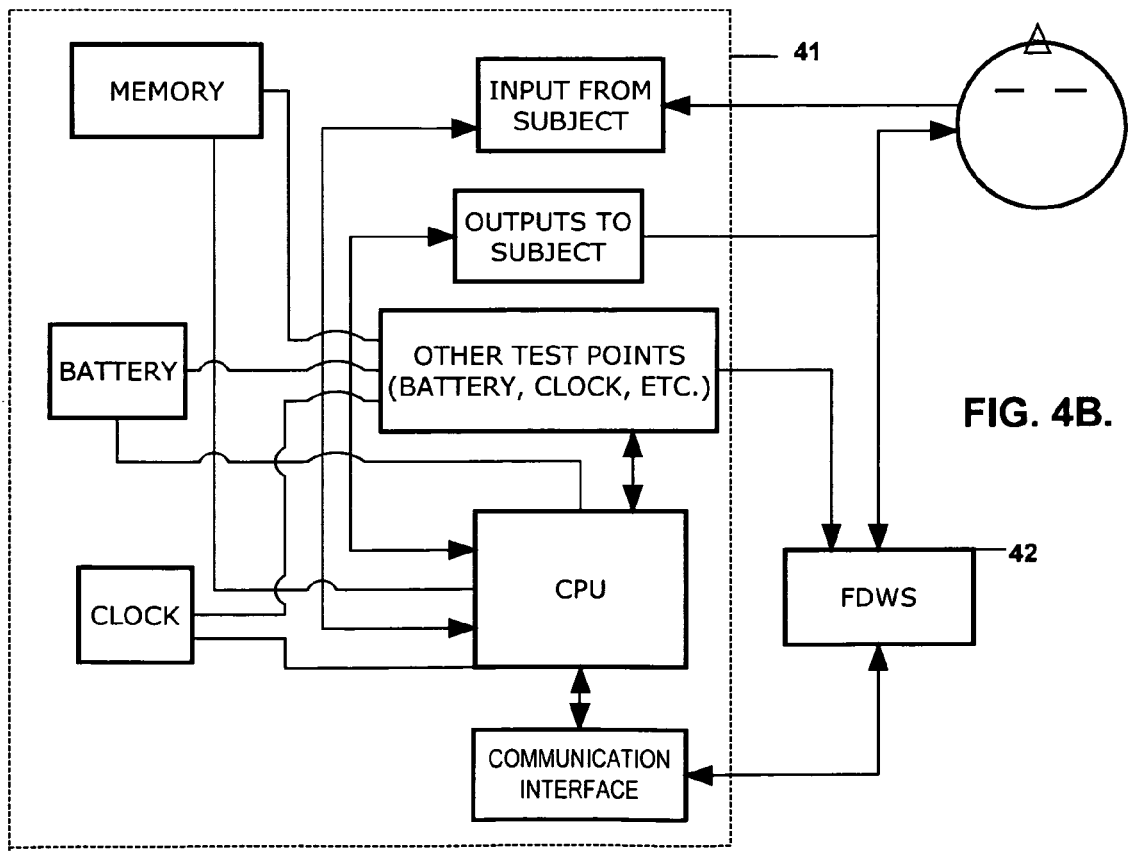
FIG. 4B depicts device failure detection wherein the failure detection and warning system interacts through an interface with a medical device being monitored.
Figure 4C:
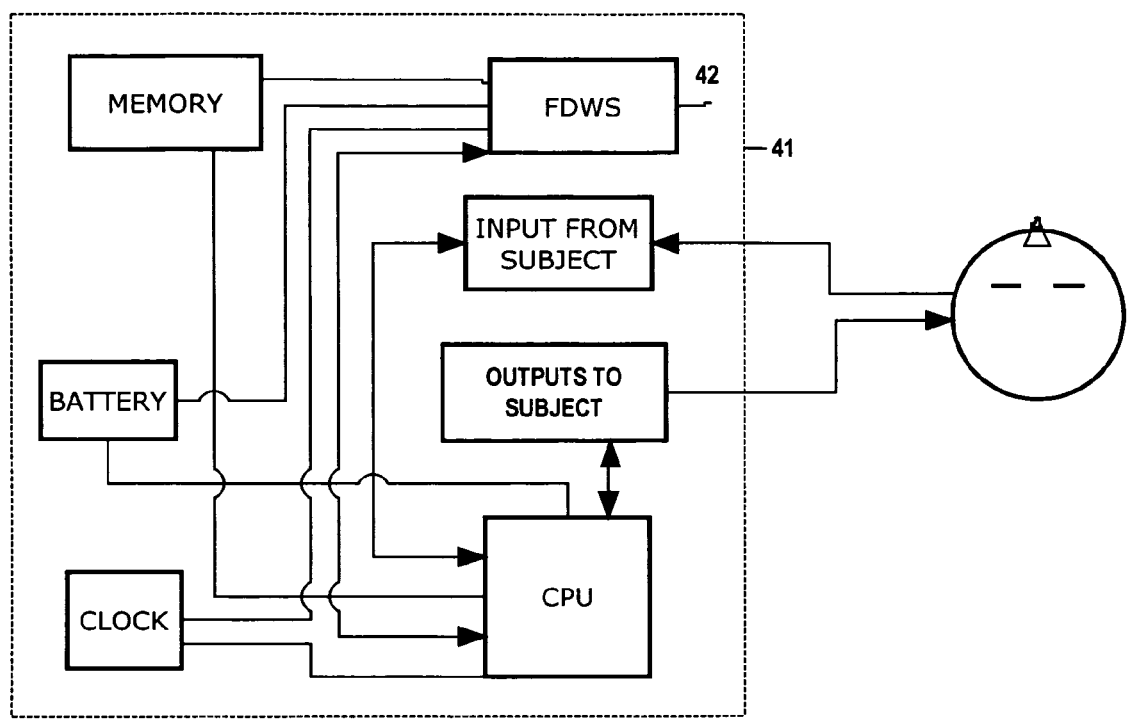
FIG. 4C depicts device failure detection wherein the failure detection and warning system is integrated with a medical device being monitored in accordance with the present invention.

Information in the second set (ii) can be accessed only by modifying the medical device and may require both hardware and/or software changes. For example, additional test points may be added or a communication interface and communication protocol may be developed between the systems to enable, e.g., interrogation by the FDWS, or event cues or programmed function changes passed by the medical device to the FDWS. FIG. 4 illustrates these situations. In FIG. 4A, the FDWS 42 uses information that is readily accessible to it from the medical device 41 and monitors, logs, and/or warns of adverse events as they occur. In FIG. 4B, the FDWS interacts with the medical device through a specific communication interface that is added to give the FDWS access to the information about the medical device for monitoring purposes, in addition to that information originally accessible in the absence of this specific communication interface. The interface in the medical device has the ability to obtain information about the status of different subsystems and functions of the medical device including, but not limited to, the battery, system status flags, and output. In this mode, the FDWS can send a command to the medical device and then wait for a reply. If the response is unexpected or if there is no response at all, the FDWS gives an alarm and can further program the medical device. Additionally, in another embodiment, a central processing unit of the medical device can trigger the FDWS to perform a sequence of tasks to sense or record the outputs of the medical device. FIG. 4C depicts an embodiment of the present invention wherein the FDWS is a part of the medical device. In this embodiment, the FDWS may be a separate module, housed in the same enclosure as the medical device and/or its features and functions may be incorporated into the design of the medical device in which case there would be no need for a separate FDWS module. Further, the FDWS may share some resources with the medical device, e.g., battery or clock, while monitoring the status of the outputs, clock, battery, memory, etc. However, a certain important functionality of the FDWS described herein, such as the software key used in programming and redundant or backup power supply to the FDWS, may be incorporated into the medical device to effect in the medical device a built-in resistance to failure and enable warning or corrective action should a failure occur.

One critical aspect of this invention is to make not only existing medical devices, but also those subsequently developed, safer. Those skilled in the art will understand that there are design and engineering differences in how this objective will be accomplished in the case of existing vs. subsequently developed devices. In the case of existing medical devices the FDWS will most typically be external to, and separate from, the medical device and may lack direct access (e.g. via ports or test points/pins) to the medical device. With subsequently developed medical devices, more design options will be available and the decision as to the placement of the FDWS in reference to the medical device, for example inside the same case or in separate cases, utilizing wired or wireless communication between the medical device and the FDWS, etc., will be implemented on performance, manufacturing, ergonomics, cost and other considerations.

Figures 5A, 5B:
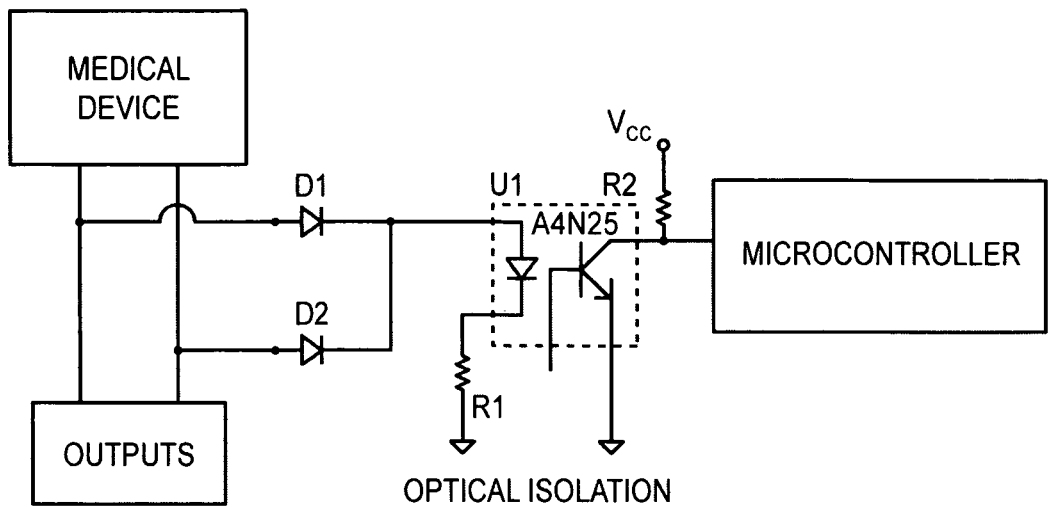

FIG. 5 A-D show circuit designs that serve as examples of some of the ways in which the FDWS can monitor a medical device and issue an alarm in the case of accidental failure according to the present invention. FIG. 5A illustrates a sample circuit to monitor a medical device that has either periodic or continuous outputs and detects disruptions from the programmed behavior of the medical device. This circuit is shown as directly tapping into the outputs of the medical device; however, if the medical device is endowed with a hardware or software interface, this or other circuits depicted herein that do not require a specific communication interface between the FDWS and medical device may be used for monitoring purposes. For example, the FDWS can use the electrical/electromagnetic artifact generated by continuous or periodic electrical stimulation to monitor the medical device and issue an alarm if this artifact either ceases to occur (in the case of continuous stimulation) or does not appear in a timely manner (in the case of periodic stimulation). Other observable noise generated when the medical device is ON may also be used for monitoring the medical device. The FDWS functions as follows:

1) The FDWS is turned ON and programmed with information regarding mode of output (periodic vs. continuous), length of stimulation period, and other relevant information about the medical device.

2) In the case of periodic output, a timer that matches the time period of therapy delivery (or of some other output) of the medical device is started. For medical devices with continuous outputs, this and the subsequent step are not required.

3) FDWS waits in standby mode (low power) until the timer goes off.

4) FDWS checks for output from the medical device. If there is an output, it goes back to standby and waits for a pre-specified time, e.g., 5 seconds. Otherwise it issues a warning. In the case of a medical device with continuous output, the FDWS will issue a warning immediately when the output accidentally stops.

Figure 5C:
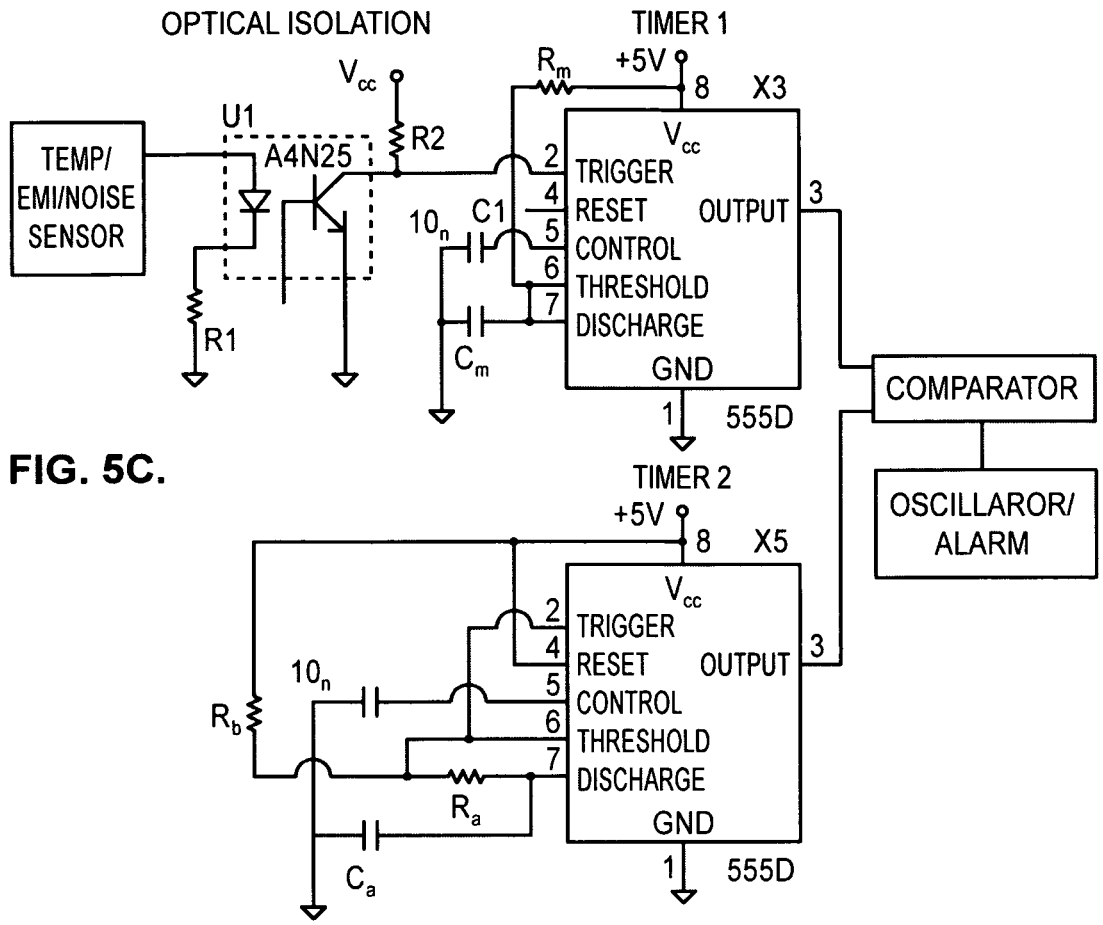
Figure 5D:
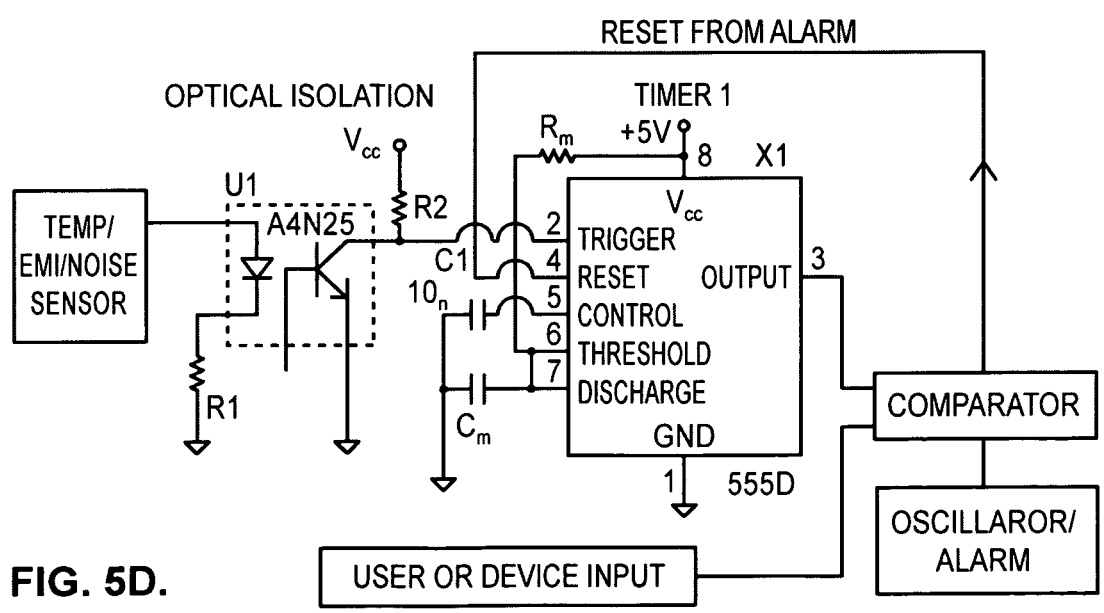

One skilled in the art will appreciate that this example can be extended to the case of non-periodic intermittent medical device output monitoring by the FDWS, provided only that the FDWS knows when the detectable medical device output is scheduled to take place. FIG. 5B illustrates a case similar to FIG. 5A with the exception that the FDWS receives additional specific information from the medical device and then performs the tasks outlined in FIG. 5A. FIG. 5C illustrates another FDWS embodiment that utilizes a simple hardware circuit to monitor a medical device that provides periodic stimulation. In this example, the FDWS is triggered by a sensor (sensing, for example, an electrical/electromagnetic artifact, or change in temperature, or in acoustic activity in the medical device), which is used to start a pulse of specific duration using Timer1 (e.g., LM555) in monostable (one shot) operation. That is, the output of Timer1 will become HIGH and remain high for the duration of the output of the medical device, such as delivery of electrical stimulation. This output of Timer1 is then compared with the output of a reference Timer2 operated in an astable operation (i.e., running as an oscillator programmed with a period equal to the time between the starts of two sets of stimulation). Whenever the output of Timer1 indicates that the stimulation did not occur as programmed (i.e., when Timer2 output goes LOW), the comparator will enable an oscillator and an alarm will be issued. FIG. 5D illustrates an FDWS circuit that can be used to monitor a medical device that provides closed-loop, or contingent (only in response to a prespecified cue or event) therapy. In this example, the FDWS may utilize manual user input (for example, pressing an event button) to command the FDWS to check whether therapy was actually delivered in response to an event of which the user was aware. The delay of Timer1 in this example is chosen to be a few minutes for the user to recognize Table 2 is a list of warnings and actions by the FDWS.

| Alarms | Actions |
| --- | --- |
| Visible - e.g., One or more LEDs | Monitors/senses/interrogates Power & Output status, medical device parameters, functions, tasks, presence of electromagnetic interference |
| Audible - e.g., Beep (One or more frequencies & loudness) | |
| Tactile - e.g., Vibrate (One or more frequencies & intensity), Heat, Tickler stimulation | Battery System BUS for activity Assess medical device temperature Signal input (e.g., EKG, EEG) |
| Other - e.g., Wireless communication | Generate one of the Alarms Call 911 Communicate to a health care representative Start an auxiliary resource (eg., back-up battery) Reset of the medical device | the event and then press an event button. This event button may be replaced by a direct input from the medical device or from the site to where therapy is being delivered. For example, sensors placed near the therapy target may be used to detect the actual therapy (based on the chemical or physical properties of the actual therapy) or on changes in tissue properties or behavior closely temporally correlated with delivery of such therapy. The monitoring of the medical device by the FDWS may also use statistical information such as time-varying probability distributions of previously detected and/or treated events to issue warnings when the period without therapy delivery exceeds a prespecified duration. In this case, the warnings may be probabilistic, that is, they may be issued with an estimated probability of failure, or when probability of failure exceeds a threshold, a feature that may conserve energy. The alarm circuit in this case has the ability to reset the Timer 1 if the circuit determines that the medical device generated the output as required. Those skilled in the art will appreciate that similar circuits with appropriate modifications can be designed for use with other medical devices, such as for drug delivery devices. A list of warnings and actions provided by the FDWS is shown in Table 2.

The FDWS may consist of hardware, software, and firmware components, or a combination thereof. The hardware components may be digital, analog, or a hybrid combination of both. Embodiments with a microprocessor, Floating Point Gate Array, or a DSP can be easily realized.

The following three examples illustrate how the FDWS may be used to monitor: (1) a medical device that contains a communication interface between the FDWS and itself that augments the set of information accessible to the FDWS, and (2) a medical device that does not contain such a communication interface, thereby restricting the set of information the FDWS may monitor. It is to be understood that the following examples are illustrations of the present invention as described herein and are not intended to be limiting as to the applicability of the present invention.

EXAMPLE 1

In this example, the FDWS is connected to a medical device via a communication interface in a bi-directional configuration, e.g., via conductors, optical fibers, or telemetry. The FDWS contains a real-time clock and issues a status request to the medical device every ten minutes, which is received via a communications port of the medical device. This action by the FDWS is automatically enabled as soon as the medical device is powered on, and every time the medical device is reset. If not in a failure state, the medical device usually returns an acknowledgment to the FDWS. If, on the other hand, the medical device does not properly acknowledge or respond to the FDWS query within a specified period of time, e.g., one-half second, or the response does not conform to requirements, the FDWS determines that the medical device may be in a fault state. In this case, the FDWS may re-send a query or status request. After "N" successive failures to receive an acknowledgment indicative of normal operational status, the FDWS determines that a fault has occurred and issues a warning and/or logs the fault. In this example, "N" may be any integer greater than or equal to "one," with "one" corresponding to no retries after first failure to receive an acknowledgment before a fault is declared and warnings issued. In addition to the default action, other actions can be programmed into the FDWS by the user, such as checking for differences between programmed therapy versus delivered therapy parameters.

EXAMPLE 2

If the FDWS is designed to simply monitor an existing medical device without modifying the medical device to add a communication interface between it and the FDWS, the FDWS would only be able to observe a limited set of information from which it must deduce the state of function of the medical device in order to infer failure. For example, the FDWS may be placed in close proximity to or contiguous with a medical device, such as a nerve stimulator that has been programmed to deliver currents to a nervous structure in an open-loop mode every ten minutes for thirty seconds. In this example, the FDWS can be configured with a clock/timer and one or more sensors to detect the presence of the field associated with electrical currents delivered by the medical device and verify that these stimulations are being delivered on schedule and for the prescribed duration, frequency and intensity. Each time the start of a stimulus train is detected, the FDWS checks the reading of this internal timer to verify whether or not the elapsed time from the end of the previous stimulation to the start of the next train differs significantly from the expected nine minutes and thirty seconds. If the difference is significant, e.g., more than one second, then one type of failure, corresponding to duration of inter-stimulus interval, is detected and a warning of some type or intensity is issued. If the timer expires after, e.g., nine minutes and thirty-one seconds without the FDWS detecting a stimulus train, another type of failure of the medical device is detected and a distinctive warning issued. Whenever the start of a stimulus train is detected, the internal timer can likewise be used by the FDWS together with the stimulation sensor(s) to detect the end of the stimulus train and verify that the train duration was sufficiently near the expected thirty seconds and register a fault if it was too short or exceeded the prescribed length. Any of the faults mentioned above will result in immediate warnings. In the case of closed-loop therapy devices, failure to detect delivery of therapy in response to a programmed cue or set of conditions, whose occurrence the FDWS monitors, can cause a warning to be issued immediately.

EXAMPLE 3

In this example suppose that, as in the previous example, the FDWS is designed to monitor an existing medical device without a communication interface between the medical device and the FDWS. In this example, however, do not assume anything in particular about the timing of observable outputs of the FDWS. Such may be the case, for instance, in a closed-loop therapeutic medical device that may apply electrical stimulation to tissue in response to a sensed change of state. Such devices include, but are not limited to, ventricular defibrilators acting in response to abnormal heart rhythms, or neural stimulators acting in response to detected neurological events such as epileptic seizures or acute pain. Since cardiac arrhythmias or epileptic seizures are typically aperiodic phenomena, the FDWS system can not be provided in advance with times of therapy delivery. However, in many cases, the subject using the medical device and/or an observer will be aware of the event that is to trigger output of the medical device, but may be unsure whether or not the medical device is properly producing the desired output. In such situations, the FDWS system may be configured to include an event button that the subject or observer may press when they perceive such an event, causing the FDWS to vacate a dormant state, check if delivery has occurred, issue a warning if delivery did not occur, or return to a dormant state if therapy was delivered. When the FDWS relies on event button presses, these can be logged by the FDWS system, e.g., by telemetry communication between the button and a receiver incorporated within the FDWS. The FDWS can time-stamp the button press and compare these times against sensed output from the medical device, which it can also time-stamp as described herein. Comparisons between the two sets of times can provide the subject/user with confirmation that their medical device is functioning properly, or can be used to determine potential failure of the medical device. Such failures could include false negatives in the detection of physiologic events that the medical device was designed to treat. Depending upon the particular application, such determinations can result in a warning to the user, logging for eventual medical device evaluation, or other action.

One skilled in the art will appreciate that observables such as electromagnetic fields, temperature changes and acoustic activity may be effectively monitored with or without direct physical contact between the FDWS and the medical device.

Those skilled in the art will also appreciate that the functions performed by the FDWS of the present invention may be incorporated directly into a medical device without a separate and dedicated unit serving as the FDWS.

Those skilled in the art will further appreciate that the FDWS may, in turn, be monitored by another FDWS or that more than one FDWS may be used to monitor a medical device for added safety through redundancy.

It is to be understood that while certain forms of the present invention have been illustrated and described herein, it is not to be limited to the specific forms or arrangement of parts described and shown.

What is claimed and desired to be covered by Letters Patent is as follows:

1. A failure detection and warning system for monitoring a medical device, comprising one or more processors configured to passively or actively detect one or more faults occurring in the medical device being monitored, the failure detection and warning system being external to the medical device, wherein the one or more faults includes at least one of an unprogrammed shut off of the medical device being monitored or an unprogrammed shut-off of an output of the medical device being monitored by the failure detection and warning system, the one or more processors further configured to utilize a monitoring hierarchy structure, the monitoring hierarchy structure configured to include a first priority relating to the medical device being in an unprogrammed off state, the monitoring hierarchy structure further configured to include a second priority relating to an unprogrammed off state of the one or more outputs of the medical device, wherein the first priority is a higher priority than the second priority.

2. The failure detection and warning system as described in claim 1, wherein the failure detection and warning system is communicatively connected to the medical device.

3. The failure detection and warning system as described in claim 2, wherein the communicative connection is wireless.

4. The failure detection and warning system as described in claim 2, wherein the communicative connection includes at least one wire or fiber.

5. The failure detection and warning system as described in claim 1, wherein the failure detection and warning system includes electrical, electromagnetic, noise, temperature or acoustic sensors configured to sense one or more active states of the medical device.

6. The failure detection and warning system as described in claim 1, wherein the failure detection and warning system includes electrical, electromagnetic, noise, temperature or acoustic sensors configured to sense one or more outputs of the medical device.

7. The failure detection and warning system as described in claim 1, wherein the failure detection and warning system includes at least one circuit configured to detect a presence of activity in the medical device.

8. The failure detection and warning system as described in claim 1, wherein the failure detection and warning system includes components configured to operatively detect events occurring continuously in the medical device.

9. The failure detection and warning system as described in claim 1, wherein the failure detection and warning system includes components configured to operatively detect events occurring periodically in the medical device.

10. The failure detection and warning system as described in claim 1, wherein the failure detection and warning system includes components configured to operatively detect events occurring randomly in the medical device.

11. The failure detection and warning system as described in claim 1, wherein the failure detection and warning system monitors at least one medical device that is external to, portable, attached to, or implanted within a subject and wherein the medical device is used for the purpose of diagnosis, monitoring, or delivery of therapy to the subject or to detect, predict, treat, log, or quantify an occurrence of or probability of the occurrence of an event in an organ or in a body of the subject.

12. The failure detection and warning system as described in claim 1, wherein in response to a determination of the failure detection and warning system of an occurrence of an event, the failure detection and warning system is configured to operatively:
   (a) initiate a sequence of activities to determine an occurrence of an action by the medical device; and
   (b) activate an alarm, if such action by the medical device is not detected by the failure detection and warning system.

13. The failure detection and warning system as described in claim 12, wherein the event is an elapsed pre-specified period of time.

14. The failure detection and warning system as described in claim 12, wherein the action is a continuous, periodic, intermittent, randomly occurring, open-loop, or contingent action.

15. The failure detection and warning system as described in claim 1, wherein, in response to detection of an unprogrammed cessation of activity of the medical device, the failure detection and warning system is configured to operatively activate an alarm.

16. The failure detection and warning system as described in claim 15, wherein the alarm includes a beeper, a tickler stimulator, heating element, 911-calling mechanism or telemetry to a remote monitoring station.

17. The failure detection and warning system of claim 1, wherein the one or more processors is further configured to transmit a first warning associated with the first priority and a second warning associated with the second priority.

18. The failure detection and warning system of claim 17, wherein the first warning is different than a warning triggered by the medical device being in proximity to an interference source.

19. The failure detection and warning system of claim 18, wherein the second warning is different than the warning triggered by the medical device being in proximity to an interference source.

20. The failure detection and warning system of claim 17, wherein the second warning is different than a warning triggered by the medical device being in proximity to an interference source.

21. The failure detection and warning system of claim 1, wherein the failure detection and warning system is further configured to reset the medical device.

22. The failure detection and warning system of claim 1, wherein the failure detection and warning system is further configured to log one or more events associated with the medical device.

23. The failure detection and warning system as described in claim 1, wherein the failure detection and warning system further includes at least one of an electrical sensor, an electromagnetic sensor, a noise sensor, a temperature sensor, and an acoustic sensor configured to sense environmental interference.

24. A failure detection and warning system for monitoring a medical device, comprising one or more processors configured to passively or actively detect one or more faults occurring in the medical device being monitored, the failure detection and warning system being external to the medical device, wherein the one or more faults includes at least one of an unprogrammed shut off of the medical device being monitored or an unprogrammed shut-off of an output of the medical device being monitored by the failure detection and warning system, the one or more processors further configured to utilize a monitoring hierarchy structure, the monitoring hierarchy structure configured to include a first priority relating to the medical device being in an unprogrammed off state, the monitoring hierarchy structure further configured to include a second priority relating to an unprogrammed off state of the one or more outputs of the medical device, wherein the first priority is a higher priority than the second priority, the failure detection and warning system also comprising:

(a) a clock mechanism; and
(b) a memory configured to operatively log at least one detected failure of the medical device, the log including at least one of a time from the clock mechanism which is indicative of a time of a detected failure of the medical device, a type of detected failure of the medical device, a type of corrective action taken by the failure detection and warning system, a response of the medical device to the corrective action, and a time of the response of the medical device to the corrective action.

25. A failure detection and warning system for monitoring a medical device, comprising one or more processors configured to passively or actively detect one or more faults occurring in the medical device being monitored, the failure detection and warning system being external to the medical device, wherein the one or more faults includes at least one of an unprogrammed shut off of the medical device being monitored or an unprogrammed shut-off of an output of the medical device being monitored by the failure detection and warning system, the one or more processors further configured to utilize a monitoring hierarchy structure, the monitoring hierarchy structure configured to include a first priority relating to the medical device being in an unprogrammed off state, the monitoring hierarchy structure further configured to include a second priority relating to an unprogrammed off state of the one or more outputs of the medical device, wherein the first priority is a higher priority than the second priority, the failure detection and warning system also comprising an insulating element which is configured to insulate the failure detection and warning system from electromagnetic interference, or filters to protect the failure detection and warning system from electromagnetic interference.

* * * * *